United States Patent [19]

Devlin et al.

[11] Patent Number: 4,579,947

[45] Date of Patent: Apr. 1, 1986

[54] SUBSTITUTED PHENYLALKYLPIPERAZINYLPROPYL (UREAS OR THIOUREAS) USEFUL FOR TREATMENT OF IMMUNOLOGICAL, INFLAMMATORY AND ALLERGIC DISORDER

[75] Inventors: John P. Devlin, Poughkeepsie, N.Y.; Karl D. Hargrave, Brookfield Center, Conn.; Edward L. Barsumian, Danbury, Conn.; Genus J. Possanza, Ridgefield, Conn.

[73] Assignee: Boehringer Ingelheim Pharmaceuticals, Inc., Ridgefield, Conn.

[21] Appl. No.: 614,245

[22] Filed: May 29, 1984

Related U.S. Application Data

[63] Continuation-in-part of Ser. No. 504,837, Jun. 16, 1983, abandoned.

[51] Int. Cl.[4] ............... C07D 295/00; A61K 31/495
[52] U.S. Cl. ...................... 544/400; 260/243.3; 544/295; 514/255
[58] Field of Search ............... 544/400, 295; 260/243.3; 424/250; 514/255

[56] References Cited

U.S. PATENT DOCUMENTS

| | | | |
|---|---|---|---|
| 4,216,216 | 8/1980 | Weber et al. | 544/396 |
| 4,227,000 | 10/1980 | Brown | 544/321 |
| 4,477,646 | 10/1984 | Myers | 544/400 |

OTHER PUBLICATIONS

Misra et al, Chem. Abst. vol. 82, (1975) 72933x.

*Primary Examiner*—Donald G. Daus
*Assistant Examiner*—Cecilia Shen
*Attorney, Agent, or Firm*—Alan R. Stempel; David E. Frankhouser; Charles J. Herron

[57] ABSTRACT

Compounds of the formula

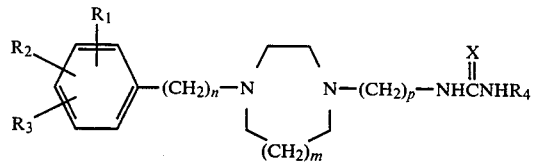

having activity as antihistamine or inhibitors of mediator release from basophils or mast cells.

41 Claims, No Drawings

SUBSTITUTED PHENYLALKYLPIPERAZINYLPROPYL (UREAS OR THIOUREAS) USEFUL FOR TREATMENT OF IMMUNOLOGICAL, INFLAMMATORY AND ALLERGIC DISORDER

This is a continuation-in-part of copending application Ser. No. 504,837. filed June 16, 1983, now abandoned.

This invention relates to novel substituted phenylalkyl(piperazinyl or homopiperazinyl)propyl-(ureas and thioureas) and non-toxic acid addition salts thereof, to methods of preparing these compounds, to pharmaceutical compositions containing them as active ingredients and to a method of using them for the treatment of immunological, inflammatory and allergic disorders.

THE PRIOR ART

German Offenlegungsschrift No. 2,727,469 (1978) [Chem. Abs., 90, 186989r (1979)] discloses, among others, 3-substituted-1-phenylpiperazinylpropyl-ureas, which are useful as intermediates in the synthesis of 1-phenylpiperazinylpropyl hexahydropyrimidine-diones, which in turn are useful as serotonin antagonists and inhibitors of thrombocyte aggregation.

THE INVENTION

More particularly, the invention relates to a novel class of phenylalkyl(piperazinyl or homopiperazinyl)-propyl-(ureas or thioureas) represented by the formula

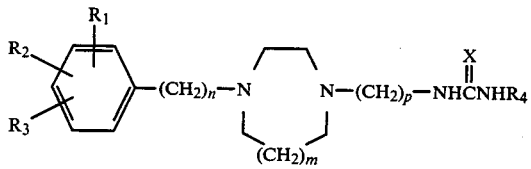

(I)

wherein
$R_1$, $R_2$, and $R_3$ are each independently hydrogen, lower alkyl, hydroxyl, lower alkoxy, lower alkylthio lower alkanoyloxy, lower alkanoyl, halogen, nitro, cyano, lower alkoxycarbonyl, di(lower alkyl)amino or trihalomethyl;
$R_4$ is hydrogen, alkyl of 1 to 12 carbon atoms, cycloalkyl of 3 to 8 carbon atoms, allyl, phenyl, or phenyl substituted by lower alkyl, halogen, lower alkoxy, carboxyl, lower alkoxycarbonyl, lower alkoxyethoxycarbonyl, cyano, nitro, lower alkylthio, di(lower alkyl)aminoethoxycarbonyl, lower alkylsulfonyl, lower alkylsulfinyl, carbamyl, tetrazolyl, sulfamyl, hydroxyl, or lower alkanoyl;
n is 1, 2, 3, or 4;
m is 0 or 1;
p is 2, 3, or 4; and
X is oxygen or sulfur;
or a non-toxic, pharmacologically acceptable acid addition salt thereof.

As used herein either alone or in combination, the term "lower alkyl" means a straight or branched, saturated hydrocarbon group having from 1 to 4 carbon atoms, for example, methyl, ethyl, propyl, isopropyl, butyl, isobutyl, or tertiary butyl. The term "halogen" means fluorine, chlorine, bromine, and iodine. The term "lower alkoxy" means a straight or branched saturated aliphatic ether group containing from 1 to 4 carbon atoms, for example, methoxy, ethoxy, propoxy, and butoxy. The term "lower alkanoyl" means an acyl residue derived from a straight or branched saturated aliphatic carboxylic acid containing from 1 to 4 carbon atoms, such as formyl, acetyl, propionyl. The term "lower alkanoyloxy" means a lower alkanoyl residue having from 1 to 4 carbon atoms attached to an oxygen function, such as acetoxy and propionyloxy. The term "lower alkoxycarbonyl" means an esterified carboxy group of the formula $R_5-OCO-$, wherein $R_5$ is a straight or branched alkyl group having 1 to 4 carbon atoms, such as methoxycarbonyl, ethoxycarbonyl, propoxycarbonyl, butoxycarbonyl. The term "lower alkoxyethoxycarbonyl" means a group of the formula $R_5-OCH_2CH_2OCO-$, wherein $R_5$ is methyl or ethyl. The term "di(lower alkyl)aminoethyl" means a group of the formula $(R_7)_2NCH_2CH_2-$, wherein $R_7$ is methyl or ethyl. The terms "lower alkylthio", "lower alkyl sulfonyl", and "lower alkyl sulfinyl", mean respectively, a group of the formula $R_8S-$, $R_8SO_2$, and $R_8SO-$, wherein $R_8$ is a straight or branched alkyl group having 1 to 4 carbon atoms.

It will be understood by those skilled in the art that the groups represented by $R_1$, $R_2$, and $R_3$ in formula I may be identical to each other or they may be different from each other. The groups represented by $R_1$, $R_2$, and $R_3$ may be substituted at any available position of the phenyl ring. However, the compounds wherein one of the groups represented by $R_1$, $R_2$, and $R_3$ is present in the para-position are preferred. Also preferred are the compounds wherein $R_2$ is hydrogen, $R_3$ is a group other than hydrogen, and $R_1$ is a group other than hydrogen substituted in the para-position. Most preferred are the compounds wherein $R_2$ and $R_3$ are each hydrogen and $R_1$ is a group other than hydrogen substituted at the para-position. The compounds wherein $R_2$ and $R_3$ are hydrogen and $R_1$ is chlorine, preferably substituted at the para-position, are most preferred. When $R_4$ in formula I is a substituted phenyl moiety, the phenyl ring may contain one or two substituents located at any available position of the phenyl ring, except that when $R_4$ is phenyl substituted by lower alkoxycarbonyl or carboxyl, said substituents cannot be located at the ortho-position of the phenyl ring.

It will be appreciated by those skilled in the art that, when m in formula I is 0, the compounds of formula I are the piperazines of the formula:

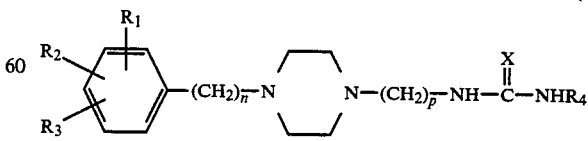

(Ia)

wherein $R_1$, $R_2$, $R_3$, $R_4$, X, n, and p have the meanings hereinbefore defined. When m in formula I is 1, the compounds of formula I are the homopiperazines of the formula:

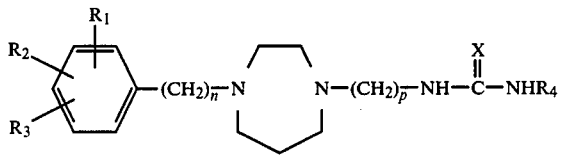

(Ib)

wherein R₁, R₂, R₃, R₄, X, n, and p have the meanings hereinbefore defined. The piperazine compounds of formula Ia are preferred.

In subgeneric aspects, the invention comprehends the following classes of compounds or a non-toxic pharmaceutically acceptable salt thereof:

(a) A compound of formula Ia or Ib wherein
R₁, R₂, and R₃ are each independently hydrogen, lower alkyl, hydroxyl, lower alkoxy, lower alkanoyloxy, lower alkanoyl, halogen, nitro, cyano, lower alkoxycarbonyl, di(lower alkyl)amino or trihalomethyl;
R₄ is hydrogen, alkyl of 1 to 12 carbon atoms, cycloalkyl of 3 to 8 carbon atoms, phenyl or phenyl substituted with lower alkyl, halogen, lower alkoxy, carboxyl, lower alkoxycarbonyl, cyano or nitro;
n is 1, 2, 3, or 4;
p is 3; and
X is oxygen or sulfur;

(b) A compound of formula Ia or Ib wherein
R₁ is chlorine;
R₂ and R₃ are each hydrogen;
R₄ is hydrogen, alkyl or 1 to 12 carbon atoms, cycloalkyl of 3 to 8 carbon atoms, allyl, phenyl, or phenyl substituted by lower alkyl, halogen, lower alkoxy, carboxyl, lower alkoxycarbonyl, lower alkoxyethoxycarbonyl, cyano, nitro, lower alkylthio, di(lower alkyl)aminoethoxycarbonyl, lower alkylsulfonyl, lower alkylsulfinyl, carbamyl, tetrazolyl, sulfamyl, hydroxyl, or lower alkanoyl;
n is 1;
p is 3; and
X is oxygen or sulfur;

(c) A compound of the formula

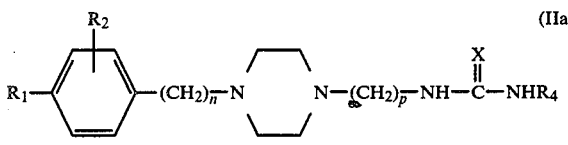

(IIa)

or

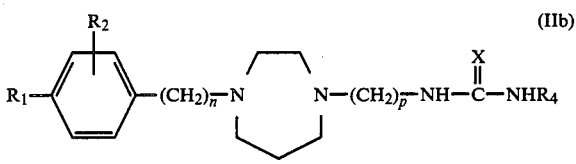

(IIb)

wherein
R₁ and R₂ are each independently hydrogen, lower alkyl, hydroxyl, lower alkoxy, lower alkylthio, lower alkanoyloxy, lower alkanoyl, halogen, nitro, cyano, lower alkoxycarbonyl, di(lower alkyl)amino, or trihalomethyl;
R₄ is hydrogen, alkyl of 1 to 12 carbon atoms, allyl, cycloalkyl of 3 to 8 carbon atoms, phenyl, or phenyl substituted by lower alkyl, halogen, lower alkoxy, carboxyl, lower alkoxycarbonyl, lower alkoxyethoxycarbonyl, cyano, nitro, lower alkylthio, di(lower alkyl)aminoethoxycarbonyl, lower alkylsulfonyl, lower alkylsulfinyl, carbamyl, tetrazolyl, sulfamyl, hydroxyl, or lower, alkanoyl;
n is 1, 2, 3, or 4;
p is 2, 3, or 4; and
X is oxygen or sulfur;

(d) A compound of formula IIa or IIb wherein
R₁ and R₂ are each independently hydrogen, lower alkyl, hydroxyl, lower alkoxy, lower alkanoyloxy, lower alkanoyl, halogen, nitro, cyano, lower alkoxycarbonyl, di(lower alkyl)amino, or trihalomethyl;
R₄ is hydrogen, alkyl of 1 to 12 carbon atoms, cycloalkyl of 3 to 8 carbon atoms, phenyl, or phenyl substituted with lower alkyl, halogen, lower alkoxy, carboxyl, lower alkoxycarbonyl, cyano, or nitro;
n is 1, 2, 3, or 4;
p is 3; and
X is oxygen or sulfur;

(e) A compound of formula IIa or IIb wherein
R₁ is chlorine;
R₂ is hydrogen;
R₄ is hydrogen, alkyl of 1 to 12 carbon atoms, cycloalkyl of 3 to 8 carbon atoms, allyl, phenyl, or phenyl substituted by lower alkyl, halogen, lower alkoxy, carboxyl, lower alkoxycarbonyl, lower alkoxyethoxycarbonyl, cyano, nitro, lower alkylthio, di(lower alkyl)aminoethoxycarbonyl, lower alkylsulfonyl, lower alkylsulfinyl, carbamyl, tetrazolyl, sulfamyl, hydroxyl, or lower alkanoyl;
n is 1;
p is 3; and
X is oxygen or sulfur;

(f) A compound of formula IIa or IIb wherein
R₁ is chlorine;
R₂ is hydrogen;
R₄ is phenyl substituted by halogen, lower alkyl, lower alkoxy, carboxyl, lower alkoxycarbonyl, lower alkoxyethoxycarbonyl, cyano, nitro, lower alkylthio, di(lower alkyl)aminoethoxycarbonyl, lower alkylsulfonyl, lower alkylsulfinyl, carbamyl, tetrazolyl, sulfamyl, hydroxy, or lower alkanoyl;
n is 1;
p is 3; and
X is oxygen;

(g) A compound of formula IIa or IIb wherein
R₂ is hydrogen;
R₃ is chlorine;
R₄ is phenyl substituted by carboxyl or lower alkoxycarbonyl;
n is 1;
p is 3; and
X is oxygen.

In the compounds above described, the compounds wherein X is oxygen are preferred. The compounds wherein n is 1 and/or p is 3 are preferred. When R₄ in the compounds above described is a lower alkyl group, the preferred chain length of the alkyl group is from 1 to 6 carbon atoms.

The compounds embraced by formula I may be prepared by the following methods.

Method A

Reaction of a compound of the formula

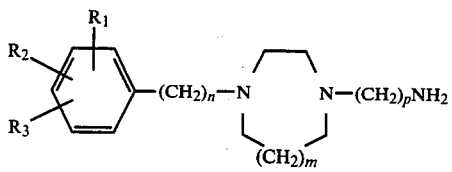 (II)

wherein $R_1$, $R_2$, $R_3$, p, n and m have the meanings previously defined, with a compound of the formula $$R_4-N=C=X \quad (III)$$

wherein $R_4$ and X have the meanings previously defined.

Method B

Reaction of a compound of the formula

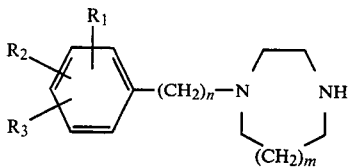 (IV)

wherein $R_1$, $R_2$, $R_3$, n and m have the meanings previously defined, with a compound of the formula

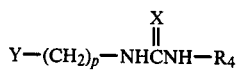 (V)

wherein $R_4$, p and X have the meanings previously defined, and Y is a reactive substituent which will react with an amine to form a carbon-nitrogen bond, for example, halogen, activated ester, hydroxyl, sulfuric ester, sulfonic ester or the like.

Method C

Reaction of a compound of the formula

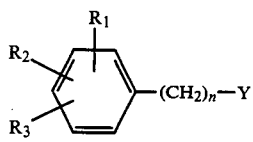 (VI)

wherein $R_1$, $R_2$, $R_3$, n and m have the meanings previously defined, with a compound of the formula

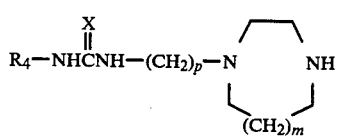 (VII)

wherein $R_4$, X, p and m have the meanings previously defined.

The reaction of method A may be performed in the presence or absence of a solvent. Aprotic organic solvents such as toluene or other hydrocarbon solvents, methylene chloride, tetrahydrofuran, dioxane, dimethylsulfoxide, or dimethylformamide may be employed. The reaction temperature depends on the starting compound and on the solvent used for the reaction and normally lies between room temperature and the reflux temperature of the mixture. The reaction time is temperature-dependent and may be several minutes to many hours. It is preferred but not essential to conduct the reaction in the presence of an acid-binding agent such as triethylamine or an alkali metal carbonate.

The reactions of methods B and C may be performed in the presence or absence of a solvent. Aqueous or organic inert solvents, depending on the nature of the reactants, may be employed. Such solvents include hydrocarbon solvents, dioxane, tetrahydrofuran, dimethylsulfoxide, dimethylformamide, ethoxyethanol and lower alkanols containing up to five carbon atoms, with or without the addition of water. It is preferred but not essential to conduct the reaction in the presence of an acid-binding agent such as triethylamine or an alkali metal carbonate.

The compounds embraced by formula I are basic and therefore form addition salts with inorganic or organic acids. Examples of non-toxic, pharmacologically acceptable acid addition salts are those formed with hydrohalic acid, especially hydrochloric or hydrobromic acid, nitric acid, sulfuric acid, o-phosphoric acid, citric acid, maleic acid, fumaric acid, propionic acid, butyric acid, acetic acid, succinic acid, methanesulfonic acid, benzenesulfonic acid, p-toluenesulfonic acid or the like.

The starting compounds for methods A through C are known compounds or may be prepared by known methods.

With the exception of the compounds wherein $R_4$ is a lower alkyl group from 7 to 12 carbon atoms, the compounds of formula I inhibit in vitro the histamine-induced contraction of isolated guinea pig ileum and are useful in warm-blooded animals for antagonizing the action of histamine at the histamine ($H_1$) receptor. Accordingly, the compounds of formula I can be employed as antihistamine agents for the treatment of allergic disorders, for example allergic rhinitis, vasomotor rhinitis, allergic conjunctivitis, hay fever, urticaria, and food allergies. Certain compounds of formula I lack the CNS side effects, such as sedation, normally associated with antihistamine therapy. In particular, 1-(3[4-(4-chlorobenzyl)piperazine-1-yl]propyl)-3-(4-carboxyphenyl)urea and 1-(3-[4-(4-chlorobenzyl)piperazin-1-yl]propyl)-3-(4-ethoxycarbonylphenyl)urea have been found not to exert significant CNS effects when tested in a standard mouse neuropharmacological profile.

With the exception of the compounds wherein $R_4$ is phenyl substituted with a carboxyl group, the compounds of formula I also inhibit in vitro the IgE mediated release of histamine from human peripheral blood leukocytes (basophils) and from rat peritoneal mast cells, and are useful in warm-blooded animals for inhibiting the antigen-induced cellular release of histamine and/or other mediators of the allergic reaction. Mediator release from basophils and mast cells has been implicated in many allergic and inflammatory disorders, such as allergic asthma, allergic rhinitis, allergic conjunctivitis, hay fever, urticaria, food allergies, and the like.

For pharmaceutical purposes the compounds of the present invention are administered to warm-blooded animals topically, perorally, parenterally or by the respiratory route as active ingredients in conventional pharmaceutical compositions, that is compositions comprising an inert pharmaceutical carrier and an effective amount of the active ingredient. The oral and the topical routes are preferred.

When the compounds of the present invention are to be administered by the oral route, they may be compounded in the form of syrups, tablets, capsules, pills and the like. Preferably, the compositions are in unit dosage form, or in form in which the patient can administer to himself a single dose. When the composition is in the form of a tablet, powder or lozenge, any pharmaceutical carrier suitable for formulating solid compositions may be used. Examples of such carriers are various starches, lactose, glucose, sucrose, cellulose, dicalcium phosphate, and chalk. The composition may also be in the form of an ingestible capsule (for instance of gelatin) containing the compound; or in the form of a syrup, a liquid solution or a suspension. Suitable liquid pharmaceutical carriers include ethyl alcohol, glycerine, saline, water, propylene glycol or sorbitol solution, which may be compounded with flavoring or coloring agents to form syrups.

The compounds of this invention may also be administered by other than the oral route. In accordance with routine pharmaceutical procedure, the compositions may be formulated, for example for rectal administration as a suppository or for presentation in an injectable form in an aqueous or non-aqueous solution, suspension or emulsion in a pharmaceutically acceptable liquid, such as sterile pyrogen-free water or a parenterally acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Such forms will be presented in dosage unit forms such as ampules or disposable injection devices, or in multi-dose vials such as a bottle from which the appropriate dose may be withdrawn, or as a solid form or concentrate which can be used to prepare an injectable formulation.

The compounds of this invention may also be suitably presented for administration to the respiratory tract as an aerosol or solution for a nebulizer, or as a microfine powder for insufflation, alone or in combination with an inert carrier such as lactose. In such a case the particles of active compounds suitably have diameters of less than 20 microns, preferably less than 10 microns. Where appropriate, small amounts of other antiallergic and antiasthmatic bronchodilators, for example sympathomimetic amines such as isoprenaline, isoetharine, metaproterenol, salbutamol, phenylephrine, fenoterol and ephedrine; xanthine derivatives such as theophylline and aminophylline; and corticosteroids such as prednisolone and adrenal stimulants such as ACTH may be included.

The compounds of this invention may also be presented as an ointment, cream, lotion, gel, aerosol or solution for topical application to the skin, nose or eye. In addition to these dosage forms a skin paint can also be formulated for application to the skin.

Topical solutions for the nose and the eye may contain, in addition to the compounds of this invention, suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chlorobutanol or phenylethyl alcohol. Topical preparations for the eye may also be presented as ointments in a suitable inert base consisting of mineral oil, petrolatum, polyethylene glycols or lanolin derivatives, along with microbial preservatives.

In any of the systemic formulations, a suitable dosage unit may contain from 1 to 500 mg of the active ingredient. A dosage unit of from 1 to 200 mg is preferred. The effective dose of the compounds of this invention depends on the particular compound employed, the nature of the condition being treated and the severity thereof, the condition of the patient, and the frequency and route of administration. In general, the systemic dosage is in the range of from about 1 to about 200 mg per day for a patient having a body weight of about 70–80 kg. A dosage range of from about 1 to about 100 mg per day is preferred.

For the topical administration, formulations containing from 0.001 to 1.0% active ingredient, preferably 0.01 to 0.1%, are preferred.

For the preparation of pharmaceutical compositions, the compounds of the present invention are mixed in the usual way with appropriate pharmaceutical carrier substances and aroma, flavoring and coloring materials and formed, for example, into tablets or capsules or, with the addition of appropriate adjuvants, suspended or dissolved in water or in an oil, for example corn oil.

The compounds of the present invention can be administered orally and parenterally in liquid or solid form. As injection medium, it is preferred to use water which contains the stabilizing agents, solubilizing agents and/or buffers conventionally used for injection solutions. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides.

Preservatives may also be added if necessary, such as benzoic acid, methyl or propyl paraben, benzalkonium chloride and other quaternary ammonium compounds.

Solid carrier material which can be used include, for example, starch, lactose, mannitol, methyl cellulose, microcrystalline cellulose, talc, silica, dibasic calcium phosphate, and high molecular weight polymers (such as polyethylene glycol).

Compositions suitable for oral administration can, if desired, contain flavoring and/or sweetening agents. For topical administration, the compounds according to the present invention can also be used in the form of powders or ointments, for which purpose they are mixed with, for example, powdered, physiologically compatible diluents or conventional ointment bases.

The following examples illustrate the present invention and will enable others skilled in the art to understand it more completely. It should be understood, however, that the invention is not limited solely to the particular examples given below.

EXAMPLE 1

1-{3-[4-(4-Chlorobenzyl)piperazin-1-yl]propyl}-3-cyclohexylurea dihydrochloride

A solution of 1-(3-aminopropyl)-4-(4-chlorobenzyl)-piperazine (2.0 g; 7.5 mmole) and cyclohexyl isocyanate (1.6 g; 12.8 mmole) in tetrahydrofuran (5 ml) was stirred at room temperature for 30 minutes. The reaction mixture was evaporated under reduced pressure, and the residual oil was dissolved in ethanol (10 ml). The crude product was precipitated as a white solid by the addition of water, collected by filtration and recrystallized twice from cyclohexane to yield 1-{3-[4-(4-chlorobenzyl)piperazin-1-yl]propyl}-3-cyclohexylurea (1.62 g; 56% yield) as a white crystalline solid, m.p. 109°–112° C. This product in methylene chloride (20 ml) was precipitated as the dihydrochloride by the addition of excess anhydrous hydrogen chloride. Recrystallization from water provided the title compound as colorless crystals, m.p. 184°–187° C.

EXAMPLE 2

1-{3-[4-(4-Chlorobenzyl)piperazin-1-yl]propyl}-3-methylurea dihydrochloride

A solution of 1-(3-aminopropyl)-4-(4-chlorobenzyl)piperazine (2.68 g; 10 mmole) and methyl isocyanate (0.57 g; 10 mmole) in methylene chloride (10 ml) was stirred at room temperature overnight. The reaction mixture was evaporated under reduced pressure, and the residue was chromatographed on a silica gel column (1"×24") using a methanolammonium hydroxide gradient (3–6%) with methylene chloride as the eluant. The product (1.0 g; 31% yield) was dissolved in methylene chloride/ether (1:1, 20 ml), and the solution was treated with anhydrous hydrogen chloride to precipitate the title compound as colorless crystals, m.p. 193°–207° C. (decomp.).

EXAMPLE 3

1-{3-[4-(4-Chlorobenzyl)piperazin-1-yl]propyl}-3-n-butylurea dihydrochloride hemihydrate A solution of 1-(3-aminopropyl)-4-(4-chlorobenzyl)piperazine (2.67 g; 10 mmole) in methylene chloride (50 ml) was refluxed for two hours with n-butyl isocyanate (1.09 g; 11 mmole). The reaction mixture was concentrated in vacuo, and the residue was treated with ethereal hydrogen chloride. Recrystallization of the precipitate from methylene chloride/methanol provided with title compound as colorless crystals (3.2 g; 71% yield), m.p. 222°–223° C.

EXAMPLE 4

1-{3-[4-(4-Chlorobenzyl)piperazin-1-yl]propyl}-3-n-hexylurea dihydrochloride

The procedure described in Example 3 was followed, using 1-(3-aminopropyl)-4-(4-chlorobenzyl)piperazine trihydrochloride (3.77 g; 10 mmole), tetrahydrofuran (50 ml), triethylamine (4.2 ml; 30 mmole) and n-hexyl isocyanate (1.41 g; 10 mmole). Recrystallization from ethanol provided the title compound (4.00 g; 83% yield) as colorless crystals, m.p. 214°–215° C.

EXAMPLE 5

1{3-[4-(4-Chlorobenzyl)piperazin-1-yl]propyl}-3-n-octylurea diihydrochloride

The procedure described in Example 3 was followed, using 1-(3-aminopropyl)-4-(4-chlorobenzyl)piperazine trihydrochloride (3.77 g; 10 mmole), tetrahydrofuran (50 ml), triethylamine (4.2 ml; 30 mmole) and n-octyl isocyanate (1.55 g; 10 mmole). Recrystallization from methanol/ethanol/water provided the title compound (3.1 g; 62% yield) as colorless crystals, m.p. 229°–230° C.

EXAMPLE 6

1-{3-[4-(4-Fluorobenzyl)piperazin-1-yl]propyl}-3-cyclohexylurea dihydrochloride monohydrate A solution of 1-(3-aminopropyl)-4-(4-fluorobenzyl)piperazine (2.0 g; 8 mmole) and cyclohexyl isocyanate (1.0 g; 8 mmole) in methylene chloride (20 ml) was stirred overnight at room temperature. The reaction mixture was evaporated, and the residue was mixed with ether (20 ml). The ether solution was filtered, and the filtrate was applied to a silica gel column (300 g) and developed in the same solvent. Fractions containing the product were eluted with methylene chloride/methanol/ammonium hydroxide (45:5:1), and on evaporation provided 1-{3-[4-(4-fluorobenzyl)piperazin-1-yl]propyl}-3-cyclohexylurea as a pale yellow oil (2.6 g; 85% yield). The product was dissolved in ether, precipitated with ethereal hydrogen chloride and recrystallized from ethanol to yield the title compound as colorless crystals (2.96 g; 80% yield), m.p. 203°–206° C.

EXAMPLE 7

1-{3-(4-Benzylpiperazin-1-yl)propyl]-3-cyclohexylurea dihydrochloride

A solution of 1-(3-aminopropyl)-4-benzylpiperazine (2 g; 12.9 mmole) and cyclohexyl isocyanate (1.6 g; 12.9 mmole) in methylene chloride (50 ml) was stirred overnight at room temperature. The reaction mixture was concentrated, and the crude product was precipitated as the dihydrochloride from ether in the manner described in Example 6. Recrystallization from ethanol provided the title compound as colorless crystals (3.62 g; 65% yield), m.p. 202°–213° C.

EXAMPLE 8

1-[3-(4-Benzylpiperazin-1-yl)propyl]-3-phenylurea

A solution of 1-(3-aminopropyl)-4-benzylpiperazine (3.0 g; 12.9 mmole) and phenyl isocyanate (1.54 g; 12.9 mmole) in methylene chloride (20 ml) was stirred at room temperature overnight. The reaction mixture was concentrated under reduced pressure, and the residue was crystallized from aqueous acetone to provide the title compound as colorless crystals (2.77 g; 61% yield), m.p. 45°–47° C.

EXAMPLE 9

1-{3-[4-(4-Chlorobenzyl)piperazin-1-yl]propyl}-3-phenylurea

A solution of 1-(3-aminopropyl)-4-(4-chlorobenzyl)piperazine (2.0 g; 7.5 mmole) and phenyl isocyanate (1.6 g; 13.4 mmole) in tetrahydrofuran (5 ml) was stirred at room temperature for 30 minutes. Ethanol (5 ml) was added, and the reaction mixture was stirred for 3 hours and then concentrated under reduced pressure. The residue was crystallized from aqueous ethanol to provide crude product (2.7 g). Recrystallization from the same solvent yielded the title compound as colorless crystals (0.62 g; 21% yield), m.p. 135°–137° C.

EXAMPLE 10

1-{3-[4-(4-Chlorobenzyl)piperazin-1-yl]propyl}-3-(4-chlorophenyl)urea hydrochloride The procedure described in Example 3 was followed, using 1-(3-aminopropyl)-4-(4-chlorobenzyl)piperazine (2.67 g; 10 mmole), methylene chloride (50 ml) and 4-chlorophenyl isocyanate (1.54 g; 10 mmole). Recrystallization from methanol provided the title compound (1.1 g; 25% yield) as colorless crystals, m.p. 241° C.

EXAMPLE 11

1-{3-[4-(4-Chlorobenzyl)piperazin-1-yl]propyl}-3-(4-methylphenyl)urea dihydrochloride monohydrate The procedure described in Example 3 was followed, using 1-(3-aminopropyl)-4-(4-chlorobenzyl)piperazine (2.67 g; 10 mmole), methylene chloride (50 ml) and 4-tolyl isocyanate (1.33 g; 10 mmole). Recrystallization from methanol/methylene chloride provided the title compound (0.81 g; 17% yield) as colorless crystals, m.p. 131°–132° C.

EXAMPLE 12

1-{3-[4-(4-Chlorobenzyl)piperazin-1-yl]-propyl}-3-(4-methoxyphenyl)urea hydrochloride The procedure described in Example 3 was followed, using 1-(3-aminopropyl)-4-(4-chlorobenzyl)piperazine (5.09 g; 19 mmole), methylene chloride (50 ml) and 4-methoxyphenyl isocyanate (2.83 g; 19 mmole). Recrystallization from methanol/methylene chloride provided the title compound (3.57 g; 45% yield) as orange-white crystals, m.p. 237°–238° C.

EXAMPLE 13

1-{3-[4-(4-Chlorobenzyl)piperazin-1-yl]propyl}-3-(4-ethoxycarbonylphenyl)urea hydrochloride The procedure described in Example 3 was followed, using 1-(3-aminopropyl)-4-(4-chlorobenzyl)piperazine trihydrochloride (7.54 g; 20 mmole), methylene chloride (50 ml), tetrahydrofuran (50 ml), triethylamine (8.4 ml; 60 mmole) and 4-ethoxycarbonylphenyl isocyanate (3.8 g; 20 mmole). Recrystallization from methanol provided the title compound (3.11 g; 34% yield) as colorless crystals, m.p. 233°–234° C.

EXAMPLE 14

1-{3-[4-(4-Chlorobenzyl)piperazin-1-yl]propyl}-3-(4-carboxyphenyl)urea hydrochloride A solution of 1-{3-[4-(4-chlorobenzyl)piperazin-1-yl]propyl}-3-(4-ethoxycarbonylphenyl)urea hydrochloride (2.59 g; 5.6 mmole) in methanol (75 ml) was refluxed for 8 hours with aqueous sodium hydroxide (1N; 10 ml). The reaction mixture was concentrated in vacuo, and the residue was dissolved in water. After filtration, the solution was acidified with hydrochloric acid, and the precipitated solid was collected and washed with methanol to provide the title compound (1.92 g; 80% yield) as colorless crystals, m.p. 244°–246° C.

EXAMPLE 15

1-{3-[4-(4-Chlorobenzyl)piperazin-1-yl]propyl}-3-(4-fluorophenyl)urea dihydrochloride monohydrate The procedure described in Example 3 was followed, using 1-(3-aminopropyl)-4-(4-chlorobenzyl)piperazine trihydrochloride (3.77 g; 10 mmole), methylene chloride (50 ml), tetrahydrofuran (10 ml), triethylamine (4.2 ml; 30 mmole) and 4-fluorophenyl isocyanate (1.37 g; 10 mmole). Recrystallization from methanol/methylene chloride provided the title compound (3.75 g; 76% yield) as colorless crystals, m.p. 225°–228° C.

EXAMPLE 16

1-{3-[4-(4-Chlorobenzyl)piperazin-1-yl]propyl}-3-(4-nitrophenyl)urea dihydrochloride The procedure described in Example 3 was followed, using 1-(3-aminopropyl)-4-(4-chlorobenzyl)piperazine trihydrochloride (3.77 g; 10 mmole), tetrahydrofuran (50 ml), triethylamine (4.2 ml; 30 mmole) and 4-nitrophenyl isocyanate (1.64 g; 10 mmole). Recrystallization from methanol/water provided the title compound (2.79 g; 55% yield) as yellow-white crystals, m.p. 230°–231° C. (dec.).

EXAMPLE 17

1-{3-[4-(4-Chlorobenzyl)homopiperazin-1-yl]propyl}-3-cyclohexylurea dihydrochloride A solution of 1-(3-aminopropyl)-4-(4-chlorobenzyl)homopiperazine (2.16 g; 7.7 mmole) in methylene chloride (30 ml) was stirred at room temperature with cyclohexyl isocyanate (1.05 g; 8.5 mmole) for one hour. The reaction mixture was concentrated under reduced pressure to an oil which was chromatographed on silica gel (methylene chloride/methanol/ammonium hydroxide: 97/2.5/0.5) to yield 1-{3-[4-(4-chlorobenzyl)homopiperazin-1-yl]propyl}-3-cyclohexylurea as a colorless oil. This oil was dissolved in ether and precipitated with ethereal hydrogen chloride to provide the title compound (2.25 g; 61% yield) as a white crystalline solid, m.p. 167°–175° C. (dec.).

EXAMPLE 18

1-{3-[4-(4-Chlorobenzyl)homopiperazin-1-yl]propyl}-3-phenylurea dihydrochloride 1-(3-Aminopropyl)-4-(4-chlorobenzyl)homopiperazine (1.03 g; 3.7 mmole) was reacted with phenyl isocyanate (0.55 g; 4.6 mmole) in methylene chloride (15 ml) for two hours in the manner described in Example 17. The crude product was isolated, purified on silica gel and converted into the hydrochloride in analogous manner. The title compound (1.23 g; 83% yield) was obtained as colorless crystals, m.p. 125°–135° C.

EXAMPLE 19

1-{3-[4-(4-Chlorobenzyl)piperazin-1-yl]propyl}-3-cyclohexylthiourea 1-(3-Aminopropyl)-4-(4-chlorobenzyl)piperazine (5.36 g; 20 mmole) was reacted with cyclohexyl isothiocyanate (2.82 g; 20 mmole) in methylene chloride (35 ml) for two hours in the manner described in Example 17. The crude product was isolated and chromatographed on silica gel in analogous manner. The product, on recrystallization from ethanol, yielded the title compound (2.98 g; 36% yield) as colorless crystals, m.p. 127°–128° C.

EXAMPLE 20

1-{3-[4-(4-Chlorobenzyl)piperazin-1-yl]propyl}-3-phenylthiourea 1-(3-Aminopropyl)-4-(4-chlorobenzyl)piperazine (5.36 g; 20 mmole) was reacted with phenyl isothiocyanate 2.82 g; 21 mmole) in methylene chloride (35 ml) in the manner described in Example 17. The crude product was isolated and chromatographed on silica gel in analogous manner. The product crystallized from ethanol to yield the title compound (2.39 g; 30% yield) as an off-white crystalline solid, m.p. 155°–156° C.

EXAMPLE 21

1-{3-[4-(4-Chlorobenzyl)piperazin-1-yl]propyl}-3-n-hexylthiourea dihydrochloride hemihydrate A solution of n-hexyl isothiocyanate (1.57 g; 10 mmole) in methylene chloride (100 ml) was slowly added to a solution of 1-(3-aminopropyl)-4-(4-chlorobenzyl)piperazine trihydrochloride (3.77 g; 10 mmole) in methylene chloride (100 ml) and triethylamine (4.3 ml; 31 mmole). The resulting mixture was refluxed for 2 hours, washed with aqueous sodium bicarbonate, dried (sodium sulfate), filtered, and the salt was precipitated with ethereal hydrochloric acid. Recrystallization from ethanol provided the title compound (0.80 g; 16% yield) as an off-white powder, m.p. 182°–186° C.

EXAMPLE 22

1-{3-[4-(4-Chlorobenzyl)piperazin-1-yl]propyl}-3-benzylurea dihydrochloride

The procedure described in Example 21 was followed, using benzyl isocyanate (1.33 g; 10 mmole), 1-(3-aminopropyl)-4-(4-chlorobenzyl)piperazine trihydrochloride (3.77 g; 10 mmole), methylene chloride (250 ml) and triethylamine (4.3 ml; 31 mmole) to provide the title compound (3.65 g; 77% yield) as colorless crystals, m.p. 203°–206° C.

EXAMPLE 23

1-{3-[4-(4-Chlorophenethyl)piperazin-1-yl]propyl}-3-n-hexylurea dihydrochloride

A solution of n-hexyl isocyanate (1.27 g; 10 mmole) in methylene chloride (25 ml) was added to a solution of 1-(3-aminopropyl)-4-(4-chlorophenethyl)piperazine (2.82 g; 10 mmole) in methylene chloride (50 ml). The resulting mixture was refluxed for 6 hours and concentrated in vacuo to give a yellow oil which was chromatographed on silica gel (methylene chloride/methanol/ammonium hydroxide; 45/5/1). Precipitation as the dihydrochloride and recrystallization from ethanol provided the title compound (0.91 g; 19% yield) as colorless crystals, m.p. 230°–233° C.

EXAMPLE 24

1-{3-[4-(4-Chlorobenzyl)piperazin-1-yl]propyl}-3-(4-cyanophenyl)urea dihydrochloride monohydrate The procedure described in Example 21 was followed, using 4-cyanophenyl isocyanate (1.44 g; 10 mmole), 1-(3-aminopropyl)-4-(4-chlorobenzyl)piperazine trihydrochloride (3.77 g; 10 mmole), methylene chloride (75 ml) and triethylamine (4.3 ml; 31 mmole). Recrystallization from methanol/ethanol provided the title compound (3.87 g; 77% yield) as colorless crystals, m.p. 236°–238° C.

EXAMPLE 25

1-{3-[4-[3-(4-Chlorophenyl)propyl]piperazin-1-yl]propyl}-3-n-hexylurea dihydrochloride (a) Triethylamine (35 g; 35 mmole) was slowly added to a mixture of chloropropylamine hydrochloride (39 g; 0.3 mol), n-hexyl isocyanate (38.2 g; 0.3 mole) and methylene chloride (500 ml). The resulting solution was stirred for one hour, and then the solvent was removed in vacuo. The residue was treated with ether, and the colorless solid was filtered off. The ether solution was then washed with water, dried (magnesium sulfate) and concentrated to give pure 1-(3-chloropropyl)-3-n-hexylurea (57.0 g; 86% yield) as colorless crystals, m.p. 48°–50° C.

(b) A mixture of 1-(3-chloropropyl)-3-n-hexylurea (2.21 g; 10 mmole), 1-[3-(4-chlorophenyl)propyl]piperazine (2.39 g; 10 mmole), triethylamine (1.01 g; 10 mmole) and alcohol (25 ml) was refluxed for 18 hours. The cooled reaction mixture was diluted with ether and washed with water, dried (sodium sulfate) and concentrated in vacuo. The resulting yellow viscous oil was purified on a silica gel column (methylene chloride/methanol; 93:7) and precipitated with ethereal hydrochloric acid to provide the title compound (1.6 g; 38% yield) as colorless crystals, m.p. 213°–216° C.

EXAMPLE 26

1-{3-[4-(3-Trifluoromethyl-4-chlorobenzyl)piperazin-1-yl]propyl}-3-n-hexylurea dihydrochloride (a) A mixture of 1-(3-chloropropyl)-3-n-hexylurea (11.0 g; 50 mmole), piperazine (43.0 g; 500 mmole) and reagent ethanol (250 ml) was refluxed for 2 hours. The solvent was removed in vacuo, and the solid residue was dissolved in water. The resulting solution was extracted with methylene chloride, concentrated in vacuo, and the residue was chromatographed on silica gel to give 1-(3-piperazinylpropyl)-3-n-hexylurea as a light yellow oil (6.7 g; 39% yield).

(b) A mixture of 1-(3-piperazinylpropyl)-3-n-hexylurea (2.7 g; 10 mmole), 3-trifluoromethyl-4-chlorobenzyl chloride (2.29 g; 10 mmole), triethylamine (1.01 g; 10 mmole) and ethanol (30 ml) was refluxed for 3 hours. The solvent was evaporated in vacuo, and water was added to the residue. The product was extracted with ether, and the extract was dried (sodium sulfate) and concentrated. Precipitation of the oily residue with ethereal hydrochloric acid, followed by recrystallization from alcohol, provided the title compound (3.1 g; 58% yield) as colorless crystals, m.p. 216°–219° C.

EXAMPLE 27

1-{3-{4-[3-(4-Chlorophenyl)propyl]piperazin-1-yl}propyl}3-(4-cyanophenyl)urea dihydrocyloride monohydrate (a) Triethylamine (13.8 g; 137 mmole) was slowly added to a mixture of 3-chloropropylamine hydrochloride (17.8 g; 137 mmole), 4-cyanophenyl isocyanate (19.7 g; 137 mmole), and methylene chloride (200 ml). The resulting solution was stirred until the mild exothermic reaction had subsided and the solvent was removed in vacuo. The product was dissolved in ether, washed with water, dried, and part of the ether removed. The colorless crystals which precipitated out were filtered and dried to give 1-(3-chloropropyl)-3-(4-cyanophenyl)urea (17.5 g; 54% yield). A small portion of the product was recrystallized from water/acetone to give pure product, m.p. 95°–97° C.

(b) A mixture of 1-(3-chloropropyl)-3-(4-cyanophenyl)urea (3.57 g; 15 mmole), 1-[3-(4-chlorophenyl)propyl]piperazine (3.58 g; 15 mmole), triethylamine (1.52 g; 15 mmole), and ethanol (100 ml) was refluxed for 35 hours. The solvent was removed in vacuo and water added to the residue. The product was extracted with ether, dried, and concentrated in vacuo. The resulting reddish-yellow oil was purified on a silica gel column (methylene chloride/methanol 9:1) to give the product as a free base (2.8 g; 42% yield). The product was dissolved in ether and precipitated with ethereal hydrochloric acid to provide, after recrystallization from water, the title compound as colorless crystals, m.p. 219°–221° C.

EXAMPLE 28

1-{3-[4-(4-Chlorobenzyl)piperazin-1-yl]propyl}-3-allylurea dihydrochloride

A solution of triethylamine (2.0 g; 20 mmole) in methylene chloride was added dropwise to a mixture of 1-(3-amino-propyl)-4-(4-chlorobenzyl)piperazine trihydrochloride (7.54 g; 20 mmole) and allyl isocyanate (1.66 g; 20 mmole) in methylene chloride. After the addition was completed the mixture was washed with water and the solvent removed. The resulting orange oil was purified on a silica gel column (methylene chloride/methanol; 9:1), precipitated with ethereal hydrochloric acid, and recrystallized from ethanol/water to provide the title compound (2.1 g; 25% yield) as colorless crystals, m.p. 232°–234° C.

EXAMPLE 29

1-{3-[4-(4-Chlorobenzyl)piperazin-1-yl]propyl}-3-(4-acetylphenyl)urea dihydrochloride dihydrate A solution of 4-acetylphenyl isocyanate (1.61 g; 10 mmole) in methylene chloride (100 ml) was added to a solution of 1-(3-aminopropyl)-4-(4-chlorobenzyl)piperazine trihydrochloride (3.77 g; 10 mmole), methylene chloride (50 ml) and triethylamine (4.3 ml; 31 mmole). The resulting mixture was refluxed 3 hours, washed with aqueous sodium bicarbonate, dried (sodium sulfate), and the product precipitated with ethereal hydrochloric acid. Recrystallization from ethanol provided the title compound (4.13 g; 82% yield) as a white powder, m.p. >197° C. (slow dec.).

EXAMPLE 30

1-{3-[4-(4-Chlorobenzyl)piperazin-1-yl]propyl}-3-(4-ethoxyphenyl)urea dihydrochloride The procedure described in Example 29 was followed, using 4-ethoxyphenyl isocyanate (1.63 g; 10 mmole), 1-(3-aminopropyl)-4-(4-chlorobenzyl)piperazine trihydrochloride (3.77 g; 10 mmole), methylene chloride (16 ml), and triethylamine (4.3 ml; 31 mmole). Recrystallization from ethanol provided the title compound (3.42 g; 68% yield) as colorless crystals, m.p. 225°–227° C.

EXAMPLE 31

1-{3-[4-(4-Chlorobenzyl)piperazin-1-yl]propyl}-3-[4-(methylthio)phenyl]urea dihydrochloride monohydrate The procedure described in Example 29 was followed, using 4-(methylthio)phenyl isocyanate (10.0 g; 60.5 mmole), 1-(3-aminopropyl)-4-(4-chlorobenzyl)piperazine trihydrochloride (22.8 g; 60.5 mmole), methylene chloride (400 ml), and triethylamine (25.8 ml; 185 mmole). Recrystallization from methanol/water provided the title compound (27.3 g; 89% yield) as colorless crystals, m.p. 212°–214° C.

EXAMPLE 32

1-{3-[4-(4-Chlorobenzyl)piperazin-1-yl]propyl}-3-(2-chlorophenyl)urea dihydrochloride monohydrate The procedure described in Example 29 was followed, using 2-chlorophenyl isocyanate (1.54 g; 10 mmole), 1-(3-aminopropyl)-4-(4-chlorobenzyl)piperazine trihydrochloride (3.77 g; 10 mmole), methylene chloride (50 ml) and triethylamine (4.3 ml; 31 mmole). Recrystallization from methanol provided the title compound (2.63 g; 53% yield) as colorless crystals, m.p. 222°–224° C.

EXAMPLE 33

1-{3-[4-(4-Chlorobenzyl)piperazin-1-yl]propyl}-3-(2,6-dichlorophenyl)urea dihydrochloride The procedure described in Example 29 was followed, using 2,6-dichlorophenyl isocyanate (1.88 g; 10 mmole), 1-(3-aminopropyl)-4-(4-chlorobenzyl)piperazine trihydrochloride (3.77 g; 10 mmole), methylene chloride (50 ml) and triethylamine (4.3 ml; 31 mmole). Recrystallization from methanol provided the title compound (2.75 g; 52% yield) as colorless crystals, m.p. 246°–248° C.

EXAMPLE 34

1-{3-[4-(4-Chlorobenzyl)piperazin-1-yl]propyl}-3-(n-dodecyl)urea dihydrochloride The procedure described in Example 29 was followed using n-dodecyl isocyanate (2.11 g; 10 mmole), 1-(3-aminopropyl)-4-(4-chlorobenzyl)piperazine trihydrochloride (3.77 g; 10 mmole) methylene chloride (100 ml), and triethylamine (3.03 g; 30 mmole). Recrystallization from water provided the title compound (3.21 g; 58% yield) as colorless crystals, m.p. 215°–222° C.

EXAMPLE 35

1-{3-[4-(4-Chlorobenzyl)piperazin-1-yl]propyl}-3-(4-carbamylphenyl)urea dihydrochloride A solution of 1-{3-[4-(4-chlorobenzyl)piperazin-1-yl]propyl}-3-(4-cyanophenyl)urea dihydrochloride monohydrate (10.0 g; 19.9 mmole), glacial acetic acid (120 ml), and concentrated hydrochloric acid (80 ml) was heated at 80° C. for 30 minutes. The mixture was then poured over ice, and basified with aqueous potassium hydroxide. The product was extracted with methylene chloride, dried (sodium sulfate), and the salt precipitated out ethereal hydrochloric acid. Several recrystallizations from ethanol provided the title compound (3.54 g; 38% yield) as colorless crystals, m.p. 224°–226° C.

EXAMPLE 36

1-{3-[4-(4-Chlorobenzyl)piperazin-1-yl]propyl}-3-(4-t-butylphenyl)urea dihydrochloride A solution of 3-iodopropyl isocyanate (4.22 g; 20 mmole) in ether (25 ml) was added to a solution of 4-t-butylaniline (2.98 g; 20 mmole) in ether (25 ml), and the resulting solution refluxed for 3 hours. After removal of the solvent, 4-chlorobenzylpiperazine (4.18 g; 20 mmole) in ethanol (50 ml) was added and the resulting solution refluxed for 24 hours. Aqueous sodium bicarbonate was added to the mixture and the product was extracted with methylene chloride, dried (sodium sulfate), and the salt precipitated with ethereal hydrochloric acid. Recrystallization several times with ethanol provided the title compound (3.73 g; 33% yield) as colorless crystals, m.p. 240°–241° C.

EXAMPLE 37

The following compounds may be prepared from equimolar amounts of 3-iodopropyl isocyanate, the appropriate substituted aniline, and 4-chlorobenzylpiperazine in a manner analogous to that described in Example 36:

A. 1-{3-[4-(4-Chlorobenzyl)piperazin-1-yl]propyl}-3-(3-carboxyphenyl)urea dihydrochloride.
B. 1-{3-[4-(4-Chlorobenzyl)piperazin-1-yl]propyl}-3-(3-ethoxycarbonylphenyl)urea dihydrochloride.
C. 1-{3-[4-(4-Chlorobenzyl)piperazin-1-yl]propyl}-3-(3-carbamylphenyl)urea dihydrochloride.
D. 1-{3-[4-(4-Chlorobenzyl)piperazin-1-yl]propyl}-3-(3-hydroxy-4-carbamylphenyl)urea dihydrochloride.
E. 1-{3-[4-(4-Chlorobenzyl)piperazin-1-yl]propyl}-3-(3-hydroxy-3-ethoxycarbonylphenyl)urea dihydrochloride.
F. 1-{3-[4-(4-Chlorophenyl)piperazin-1-yl]propyl}-3-(3-hydroxy-4-carboxyphenyl)urea dihydrochloride.
G. 1-{3-[4-(4-Chlorophenyl)piperazinyl-1-yl]propyl}-3-(3-methoxy-3-ethoxycarbonylphenyl)urea dihydrochloride.
H. 1-{3-[4-(4-Chlorophenyl)piperazin-1-yl]propyl}-3-(3-methoxy-4-carboxyphenyl)urea dihydrochloride.
I. 1-{3-[4-(4-Chlorophenyl)piperazin-1-yl]propyl}-3-(3-carboxy-4-hydroxyphenyl)urea dihydrochloride.
J. 1-{3-[4-(4-Chlorophenyl)piperazin-1-yl]propyl}-3-(3-ethoxycarbonyl-4-hydroxyphenyl)urea dihydrochloride.
K. 1-{3-[4-(4-Chlorophenyl)piperazin-1-yl]propyl}-3-(3-carboxy-4-methoxyphenyl)urea dihydrochloride.
L. 1-{3-[4-(4-Chlorophenyl)piperazin-1-yl]propyl}-3-(3-ethoxycarbonyl-4-methoxyphenyl)urea dihydrochloride.

EXAMPLE 38

The in vitro inhibition of histamine release from human leukocytes (basophils) and from rat peritoneal mast cells by the compounds of formula I can be demonstrated according to the following biochemical test procedures:

A. Procedure for Determining Inhibition of Human Leukocyte (Basophil) Histamine Release In Vitro 1. Separation of Leukocytes: A modification of the method of L. Lichtenstein and A. Osler, *J.Exp.Med.* 120, 507 (1964) was used. Heparinized human blood (80–100 ml) is mixed with 20 ml of saline (0.2%) containing 0.6 gm of dextrose and 1.2 gm dextran in propylene centrifuge tubes. The mixture is kept at ambient temperature for 60–90 minutes to allow the separation of erythrocytes from the platelet-leukocyte-rich supernate. The supernate is removed and centrifuged for 8 minutes at 110×g in cold. The leukocyte pellet is washed 2× with Tris buffer and finally suspended in 150–180 ml Tris-ACM buffer at 1–2×10$^6$ cells/ml.

2. Reaction Mixture: The reaction is carried out in 12×75 mm plastic tubes at a total volume of 1.25 ml. The reaction medium includes 0.05 ml rabbit anti-human IgE (the antigen), 0.2 ml of the test compound in water at concentrations ranging from 10–1000 μM, and 1.0 ml of the leukocyte suspension. The reaction mixture is incubated in a 37° C. shaking water bath for 60 minutes. Upon completion of the reaction, the tubes are centrifuged and the supernatants collected. The protein is removed from the supernatants by precipitation with 0.2 ml of 8% perchloric acid.

3. Histamine Assay: Histamine release is measured by the automated fluorometric method of W. Siraganian and W. Hook in Chapter 102 of the *Manual of Clinical Immunology*, 2nd Edition, Edited by R. Rose and H. Friedman, Published by the American Society for Microbiology, Washington, D.C. 1980. Percent inhibition is calculated as follows:

$$\frac{(\text{Control} - \text{blank}) - (\text{Test sample} - \text{blank})}{(\text{Control} - \text{blank})} \times 100$$

The concentration which causes a 50 percent inhibition (IC$_{50}$) of histamine release is interpolated from a plot of percent inhibition versus logarithm of drug concentration.

B. Procedure for Determining Inhibitors of Rat Peritoneal Mast Cell Histamine Release 1. Harvest of Peritoneal Mast Cells: After the rats are sacrificed with ether, 20 ml of Minimum Essential Medium (MEM) containing 20 units/ml heparin is injected into the peritoneum. The abdomen is massaged for one minute and the lavage fluid collected. The peritoneal cells are centrifuged at 1800 rpm for 8 minutes in cold. After two washes with Tris A buffer, the cells are resuspended in Tris ACM buffer at 2–33 10$^6$ cells/ml.

2. Reaction Mixture: The reaction is carried out in 12×75 mm plastic tubes at a total volume of 1.25 ml. The reaction mixture includes 0.5 ml (10–1000 μg) sheep anti-rat IgE or ovalbumin, 0.2 ml of the test compound in water at concentrations ranging from 10–1000 μM, 0.5 ml phosphatidylserine solution (20–60 μg to each tube), and 0.5 ml of cell suspension.

The reaction mixture is incubated in a 37° C. shaking water bath for 60 minutes. Upon completion of the reaction, the tubes are centrifuged and the supernatants collected. The protein is removed from the supernatants by precipitation with 0.2 ml of 8% perchloric acid.

3. Histamine Assay: Histamine release is measured by the automated fluorometric method of Siraganian, supra.

The concentration which causes a 50% inhibition (IC$_{50}$) of histamine release is computed as in Part A.

The results of the testing compounds of formula I for the inhibition of histamine release from human leukocytes (basophils) according to Procedure A, above, are shown in Table A.

TABLE A

| Test Compound (Example Number) | Inhibition IC$_{50}$(μM) |
|---|---|
| 1 | 50 |
| 2 | 300 |
| 3 | 50 |
| 4 | 8 |
| 5 | 16 |
| 6 | 50 |
| 7 | 240 |
| 8 | 400 |
| 9 | 78 |
| 10 | 30 |
| 11 | 37 |
| 12 | 80 |
| 13 | 190 |
| 14 | >1000 |
| 15 | 20 |
| 16 | 30 |
| 17 | 13 |
| 18 | 15 |
| 19 | 26 |
| 20 | 37 |
| 21 | Int.* |
| 22 | 112 |
| 23 | 16 |
| 24 | 81 |
| 25 | 10 |
| 26 | Int.* |
| 27 | 20 |
| 28 | 120 |
| 29 | 115 |

TABLE A-continued

| Test Compound (Example Number) | Inhibition IC$_{50}$($\mu$M) |
| --- | --- |
| 30 | 35 |

*Int. = interference with test procedure.

The results of the testing of compounds of formula I for the inhibition of histamine release from rat peritoneal mast cells according to Procedure B is shown in Table B.

TABLE B

| Test Compound (Example Number) | Inhibition IC$_{50}$($\mu$M) |
| --- | --- |
| 1 | 108 |
| 4 | 110 |
| 5 | 210 |
| 9 | >1000 |
| 24 | 150 |
| 25 | Int.* |

EXAMPLE 39

The antagonism of the effects of histamine on the contraction of isolated guinea pig ileum by the compounds of formula I can be determined by the procedure of G. Possanza, A. Bauen, and P. Stewart, *Int. Arch. Allergy Appl. Immunol.*, 49, 289 (1975). The degree of inhibition is determined as the difference between the contraction caused by histamine (final concentration 0.2 $\mu$g/ml) alone and that seen in the presence of both histamine and the test compound. The inhibitory activity of the test compound is expressed as that concentration of the compound which causes a 50% reduction of the contractile response (IC$_{50}$).

When tested according to the above procedure, compounds of formula I gave the results shown in TABLE C.

TABLE C

| Test Compound (Example Number) | Inhibition IC$_{50}$($\mu$M) |
| --- | --- |
| 1 | 0.015 |
| 2 | 0.63 |
| 3 | 0.07 |
| 4 | 0.05 |
| 5 | 0.75 |
| 6 | 0.11 |
| 7 | 0.32 |
| 8 | 0.21 |
| 9 | 0.05 |
| 10 | 0.15 |
| 11 | 0.065 |
| 12 | 0.015 |
| 13 | 0.11 |
| 14 | 0.21 |
| 15 | 0.06 |
| 16 | 0.018 |
| 17 | 0.15 |
| 18 | 0.55 |
| 19 | 0.11 |
| 20 | 0.10 |
| 21 | 0.08 |
| 22 | 0.23 |
| 23 | 0.02 |
| 24 | 0.008 |
| 25 | 0.13 |
| 26 | 0.09 |
| 27 | 0.11 |
| 28 | 0.17 |
| 29 | 0.02 |
| 30 | — |

EXAMPLE 40

Tablets

The tablet composition is compounded from the following ingredients:

| | |
| --- | --- |
| 1-{3-[4-(4-Chlorobenzyl)piperazin-1-yl]propyl}-3-(4-ethoxycarbonylphenyl)urea hydrochloride | 0.010 parts |
| Stearic acid | 0.010 parts |
| Dextrose | 1.890 parts |
| Total | 1.910 parts |

Preparation:

The ingredients are admixed in conventional manner, and the mixture is compressed into 1.91 gm-tablets, each of which is an oral dosage unit composition containing 10 mgm of the active ingredient.

EXAMPLE 41

Ointment

The ointment composition is compounded from the following ingredients:

| | |
| --- | --- |
| 1-{3-[4-(4-Chlorobenzyl)piperazin-1-yl]propyl}-3-(4-methoxyphenyl)-urea hydrochloride | 2.000 parts |
| Fuming hydrochloric acid | 0.011 parts |
| Sodium pyrosulfite | 0.050 parts |
| Mixture (1:1) of cetyl alcohol and stearyl alcohol | 20.000 parts |
| White vaseline | 5.000 parts |
| Synthetic bergamot oil | 0.075 parts |
| Distilled water | q.s.ad 100.000 parts |

Preparation:

The ingredients are uniformly blended in conventional manner into an ointment, 100 g of which contain 2.0 gm of the active ingredient.

EXAMPLE 42

Inhalation aerosol

The aerosol composition is compounded from the following ingredients:

| | |
| --- | --- |
| 1-{3-[4-(4-Chlorobenzyl)piperazin-1-yl]-propyl}-3-n-hexylurea dihydrochloride | 1.00 parts |
| Soybean lecithin | 0.20 parts |
| Propellant gas mixture (Freon 11, 12 and 14) | q.s.ad 100.00 parts |

Preparation:

The ingredients are compounded in conventional manner, and the composition is filled into aerosol containers with a metering valve which releases 0.5 to 2.0 mgm of active ingredient per actuation of the valve.

EXAMPLE 43

Hypodermic solution

The solution is compounded from the following ingredients:

| | |
| --- | --- |
| 1-{3-[4-(4 Chlorobenzyl)piperazin-1-yl]-propyl}-3-(4-carboxyphenyl)urea hydrochloride | 5.0 parts |
| Sodium pyrosulfite | 1.0 parts |

-continued

| | |
|---|---|
| Sodium salt of EDTA | 0.5 parts |
| Sodium chloride | 8.5 parts |
| Double-distilled water | q.s.ad 1000.0 parts |

Preparation:

The individual ingredients are dissolved in a sufficient amount of double-distilled water, the solution is diluted to the indicated concentration with additional double-distilled water, the resulting solution is filtered until free from suspended particles, and the filtrate is filled under aseptic conditions into 1 ml ampules which are subsequently sterilized and sealed. Each ampule contains 5 mgm of the active ingredient.

EXAMPLE 44

Topical solution (ophthalmic or nasal)

The solution composition is compounded from the following ingredients:

| | |
|---|---|
| 1-{3-[4-(4-Chlorobenzyl)piperazin-1-yl]-propyl}-3-(4-cyanophenyl)urea hydrochloride | 0.020 parts |
| Disodium hydrogen phosphate | 0.758 parts |
| Dihydrogen sodium phosphate | 0.184 parts |
| Sodium chloride | 0.365 parts |
| Polyvinyl alcohol | 3.500 parts |
| Benzalkonium chloride | 0.010 parts |
| Distilled water | q.s.ad 100.000 parts |

Preparation:

The ingredients are combined in conventional manner to form an aqueous solution. The solution is appropriately filtered, with the ophthalmic solution requiring sterile filtration. Each ml of the solution contains 0.2 mg of the active ingredient.

Any one of the other compounds embraced by formula I or a non-toxic, pharmacologically acceptable acid addition salt thereof may be substituted for the particular active ingredient in Examples 40 through 44. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

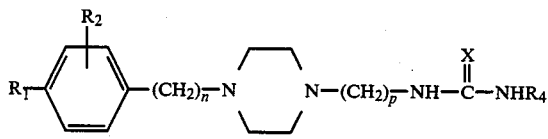

wherein:

$R_1$ and $R_2$ are each independently hydrogen, lower alkyl, hydroxyl, lower alkoxy, lower alkylthio, lower alkanoyloxy, lower alkanoyl, halogen, nitro, cyano, lower alkoxycarbonyl, di(lower alkyl)amino, or trihalomethyl;

$R_4$ is hydrogen, alkyl of 1 to 12 carbon atoms, cycloalkyl of 3 to 8 carbon atoms, allyl, phenyl, or phenyl mono- or di-substituted at any available position of the phenyl ring by lower alkyl, halogen, lower alkoxy, carboxy, lower alkoxycarbonyl, lower alkoxyethoxycarbonyl, cyano, nitro, lower alkylthio, di(lower alkyl)aminoethoxycarbonyl, lower alkylsulfonyl, lower alkylsulfinyl, carbamyl, tetrazolyl, sulfamyl, hydroxyl, or lower alkanoyl, with the proviso that when $R_4$ is phenyl substituted by lower alkoxycarbonyl or carboxyl said substituents cannot be located at the ortho-position of the phenyl ring;

n is 1, 2, 3, or 4;

p is 2, 3, or 4; and

X is oxygen or sulfur;

or a non-toxic, pharmaceutically acceptable acid addition salt thereof.

2. A compound as defined in claim 1, wherein m is 0.

3. A compound as defined in claim 2 wherein $R_1$ is chlorine;

$R_2$ is hydrogen;

$R_4$ is hydrogen, alkyl of 1 to 12 carbon atoms, cycloalkyl of 3 to 8 carbon atoms, allyl, phenyl, or phenyl mono- or di- substituted at any available position of the phenyl ring by lower alkyl, halogen, lower alkoxy, carboxyl, lower alkoxycarbonyl, lower alkoxyethoxycarbonyl, cyano, nitro, lower alkylthio, di(lower alkyl)aminoethoxycarbonyl, lower alkylsulfonyl, lower alkylsulfinyl, carbamyl, tetrazolyl, sulfamyl, hydroxyl, or lower alkanoyl, with the proviso that when $R_4$ is phenyl substituted by lower alkoxycarbonyl or carboxyl said substituents cannot be located at the ortho-position of the phenyl ring;

n is 1;

p is 3; and

X is oxygen or sulfur.

4. A compound as defined in claim 3, wherein $R_1$ is chlorine;

$R_2$ is hydrogen;

$R_4$ is hydrogen, alkyl of 1 to 12 carbon atoms, cycloalkyl of 3 to 8 carbon atoms, alkyl, phenyl or phenyl mono- or di-substituted at any available position of the phenyl ring by lower alkyl, halogen, lower alkoxy, carboxyl, lower alkoxycarbonyl, lower alkoxyethoxycarbonyl, cyano, nitro, lower alkylthio, di(lower alkyl)aminoethoxycarbonyl, lower alkylsulfonyl, lower alkylsulfinyl, carbamyl, tetrazolyl, sulfamyl, hydroxyl, or lower alkanoyl, with the proviso that when $R_4$ is phenyl substituted by lower alkoxycarbonyl or carboxyl said substituents cannot be located at the ortho-position of the phenyl ring;

n is 1;

p is 3; and

X is oxygen.

5. A compound as defined in claim 4, wherein $R_1$ is chlorine;

$R_2$ is hydrogen;

$R_4$ is phenyl mono- or di-substituted by carboxyl or lower alkoxycarbonyl, with the proviso that said substituents can be located at any available position of the phenyl ring except the ortho-position;

n is 1;

p is 3; and

X is oxygen.

6. The compound as defined in claim 2 which is 1-{3-[4-(4-chlorobenzyl)piperazin-1-yl]propyl}-3-cyclohexylurea.

7. The compound as defined in claim 2 which is 1-{3-[4-(4-chlorobenzyl)piperazin-1-yl]propyl{-3-methylurea.

8. The compound as defined in claim 2 which is 1-{3-[4-(4-chlorobenzyl)piperazin-1-yl]propyl}-3-n-butylurea.

9. The compound as defined in claim 2 which is 1-{3-[4-(4-chlorobenzyl)piperazin-1-yl]propyl}-3-n-hexylurea.

10. The compound as defined in claim 2 which is 1-{3-[4-(4-chlorobenzyl)piperazin-1-yl]propyl}-3-n-octylurea.

11. The compound as defined in claim 2 which is 1-{3-[4-(4-fluorobenzyl)piperazin-1-yl]propyl}-3-cyclohexylurea.

12. The compound as defined in claim 2 which is 1-[3-(4-benzylpiperazin-1-yl)propyl]-3-cyclohexylurea.

13. The compound as defined in claim 2 which is 1-[3-(4-benzylpiperazin-1-yl)propyl]-3-phenylurea.

14. The compound as defined in claim 2 which is 1-{3-[4-(4-chlorobenzyl)piperazin-1-yl]propyl}-3-phenylurea.

15. The compound as defined in claim 2 which is 1-{3-[4-(4-chlorobenzyl)piperazin-1-yl]propyl}-3-(4-chlorophenyl)urea.

16. The compound as defined in claim 2 which is 1-{3-[4-(4-chlorobenzyl)piperazin-1-yl]propyl}-3-(4methylphenyl)urea.

17. The compound as defined in claim 2 which is 1-{3-[4-(4-chlorobenzyl)piperazin-1-yl]propyl}-3-(4-methoxyphenyl)urea.

18. The compound as defined in claim 2 which is 1-{3-[4(4chlorobenzyl)piperazin-1-yl]propyl}-3-(4-ethoxycarbonylphenyl)urea.

19. The compound as defined in claim 2 which is 1-{3-[4-(4-chlorobenzyl)piperazin-1-yl]propyl}-3-(4-carboxyphenyl)urea.

20. The compound as defined in claim 2 which is 1-{3-[4-(4-chlorobenzyl)piperazin-1-yl]propyl}-3-(4-fluorophenyl)urea.

21. The compound as defined in claim 2 which is 1-{3-[4-(4-chlorobenzyl)piperazin-1-yl]propyl}-3-(4-nitrophenyl)urea.

22. The compound as defined in claim 2 which is 1-{3-[4-(4-chlorobenzyl)piperazin-1-yl]propyl}-3-cyclohexylthiourea.

23. The compound as defined in claim 2 which is 1-{3-[4-(4-chlorobenzyl)piperazin-1-yl]propyl}-3-phenylthiourea.

24. The compound as defined in claim 2 which is 1-{3-[4-(4-chlorobenzyl)piperazin-1-yl]propyl}-3-n-hexylthiourea.

25. The compound as defined in claim 2 which is 1-{3-[4-(4-chlorobenzyl)piperazin-1-yl]propyl}-3-benzylurea.

26. The compound as defined in claim 2 which is 1-{3-[4-(4-chlorobenzyl)piperazin-1-yl]propyl}-3-(2-chlorophenyl)urea.

27. The compound as defined in claim 2 which is 1-{3-[4-(4-chlorobenzyl)piperazin-1-yl]propyl}3-(4-cyanophenyl)urea.

28. The compound as defined in claim 2 which is 1-{3-[4-[3-(4-chlorophenyl)propyl]piperazin-1-yl]propyl}-3-n-hexylurea.

29. The compound as defined in claim 2 which is 1-{3-[4-(3-trifluoromethyl-4-chlorobenzyl)piperazin-1-yl]propyl}-3-n-hexylurea.

30. The compound as defined in claim 2 which is 1-{3-{4-[3-(4-chlorophenyl)propyl]piperazin-1-yl}propyl}-3-(4-cyanophenyl)urea.

31. The compound as defined in claim 2 which is 1-{3-[4-(4-chlorobenzyl)piperazin-1-yl]propyl}-3-allylurea.

32. The compound as defined in claim 2 which is 1-{3-[4-(4-chlorobenzyl)piperazin-1-yl]propyl}-3-(4-acetylphenyl)urea.

33. The compound as defined in claim 2 which is 1-{3-[4-(4-chlorobenzyl)piperazin-1-yl]propyl}-3-(4-ethoxyphenyl)urea.

34. The compound as defined in claim 2 which is 1-{3-[4-(4-chlorobenzyl)piperazin-1-yl]propyl}-3-[4-(methylthio)phenyl]urea.

35. The compound as defined in claim 2 which is 1-{3-[4-(4-chlorobenzyl)piperazin-1-yl]propyl}-3-(2-chlorophenyl)urea.

36. The compound as defined in claim 2 which is 1-{3-[4-(4-chlorobenzyl)piperazin-1-yl]propyl}-3-(2,6-dichlorophenyl)urea.

37. The compound as defined in claim 2 which is 1-{3-[4-(4-chlorobenzyl)piperazin-1-yl]propyl}-3-(n-dodecyl)urea.

38. The compound as defined in claim 2 which is 1-{3-[4-(4-chlorobenzyl)piperazin-1-yl]propyl}-3-(4-carbamylphenyl)urea.

39. The compound as defined in claim 2 which is 1-{3-[4-(4-chlorobenzyl)piperazin-1-yl]propyl}-3-(4-t-butylphenyl)urea.

40. An antiallergic composition comprising an inert pharmaceutical carrier and an effective antiallergic amount of a compound of claim 1.

41. The method of treating an allergic reaction in a warm-blooded animal in need thereof, which comprises perorally, parenterally, topically or by inhalation administering to said animal an effective antiallergic amount of a compound of claim 1.

* * * * *